United States Patent [19]

Linden

[11] Patent Number: 4,854,873
[45] Date of Patent: Aug. 8, 1989

[54] ORAL IMPLANT

[75] Inventor: Harry A. Linden, Santa Barbara, Calif.

[73] Assignee: Hall Surgical Division of Zimmer, Inc., Carpinteria, Calif.

[21] Appl. No.: 107,321

[22] Filed: Oct. 13, 1987

[51] Int. Cl.$^4$ ............................................... A61C 8/00
[52] U.S. Cl. ..................................... 433/173; 433/175
[58] Field of Search ............... 433/173, 174, 175, 176, 433/201.1

[56] References Cited

U.S. PATENT DOCUMENTS

| | | | |
|---|---|---|---|
| 2,258,207 | 10/1941 | Irwin | 433/173 |
| 2,449,522 | 9/1948 | White | 433/173 |
| 2,721,387 | 10/1955 | Ashuckian | 433/173 |
| 3,717,932 | 2/1973 | Brainin | 433/175 |
| 3,729,825 | 5/1973 | Linkow et al. | 433/176 |
| 3,849,887 | 11/1974 | Brainin | 433/173 |
| 3,866,321 | 2/1975 | Valen | 433/176 |
| 4,231,120 | 11/1980 | Day | 433/173 |
| 4,687,443 | 8/1987 | Driskell | 433/173 |
| 4,744,755 | 5/1988 | Ross | 433/201.1 |

Primary Examiner—John J. Wilson
Attorney, Agent, or Firm—Stuart E. Krieger

[57] ABSTRACT

The oral implant is in the shape of a cylinder with a flat proximal end and a rounded distal end. Projecting members are formed on the cylindrical surface that taper from the proximal end of the cylindrical body toward the distal end thereof. The projecting members are radially spaced, and in one embodiment have flutes formed on the tapered surface. A lateral through-hole is provided at the distal end of the cylindrical body. The proximal end includes a hexagonal-shaped recess for reception of a twisting tool. After the twisting tool is removed the hexagonal recess receives a dental prosthesis. Another embodiment of the oral implant includes radially spaced ridges that are longitudinally aligned with projecting members on quadrants of the cylindrical surface. Either embodiment of the implant member is installed by press-fitting the implant into a hole in the jawbone and then twisting the implant a predetermined amount to permit the projecting members and the ridges to breach into the bone thereby forming undercuts in the bone that rigidly lock the implant in position.

17 Claims, 4 Drawing Sheets

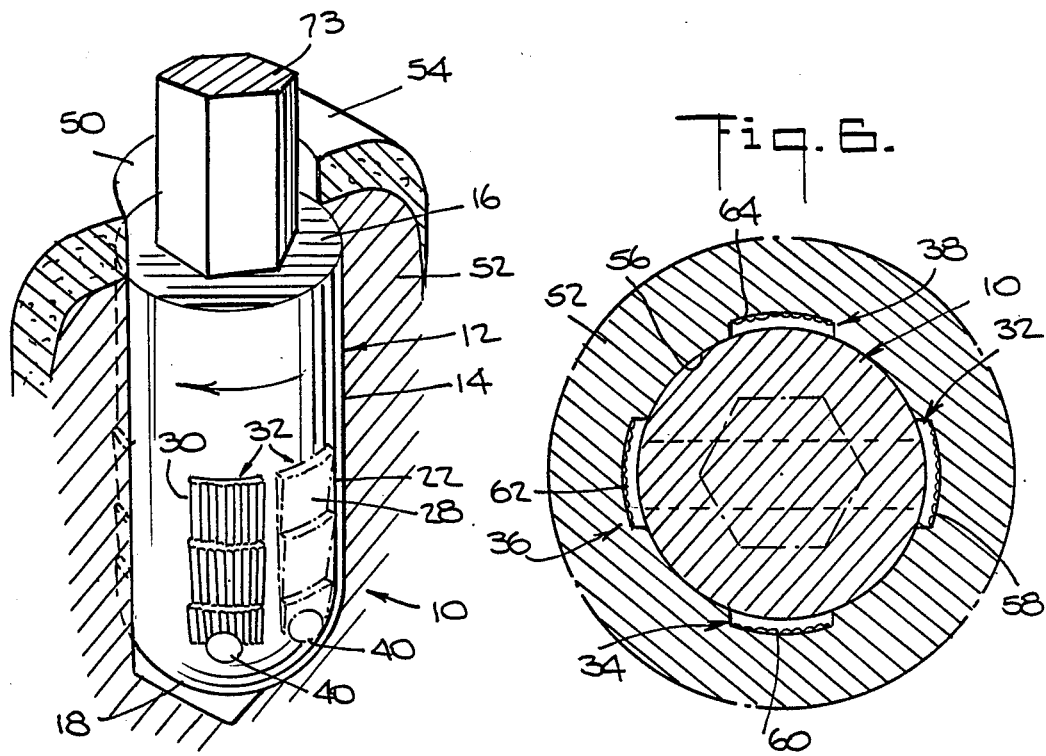

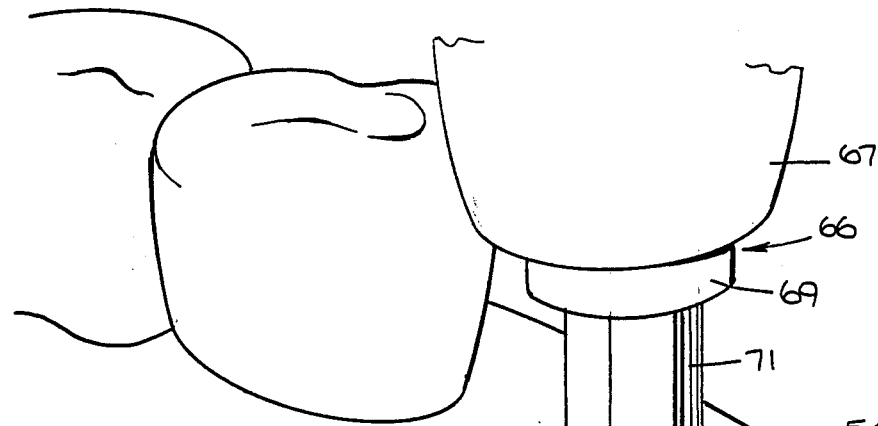
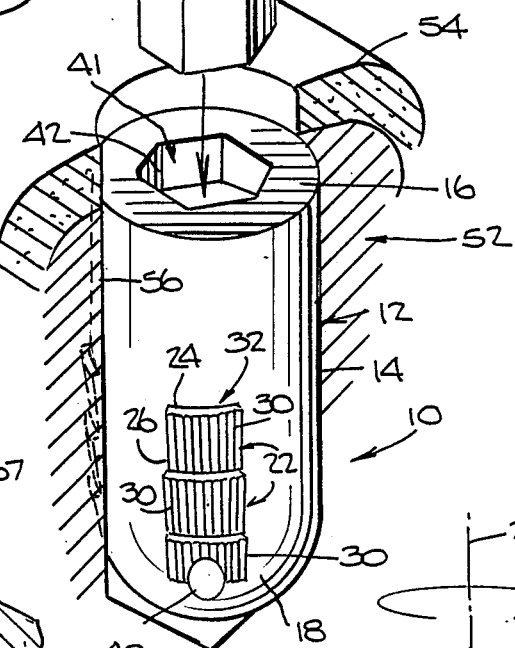
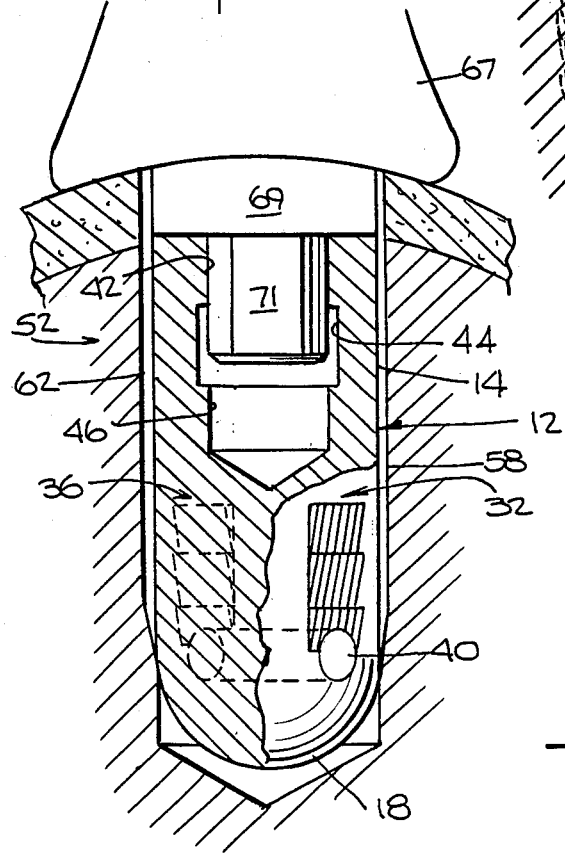
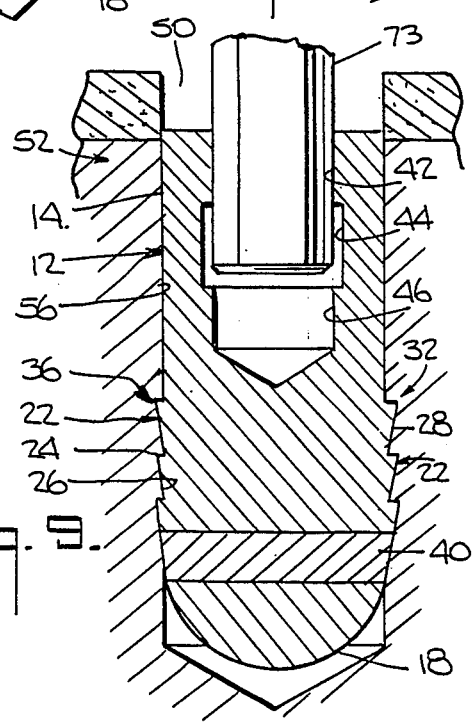

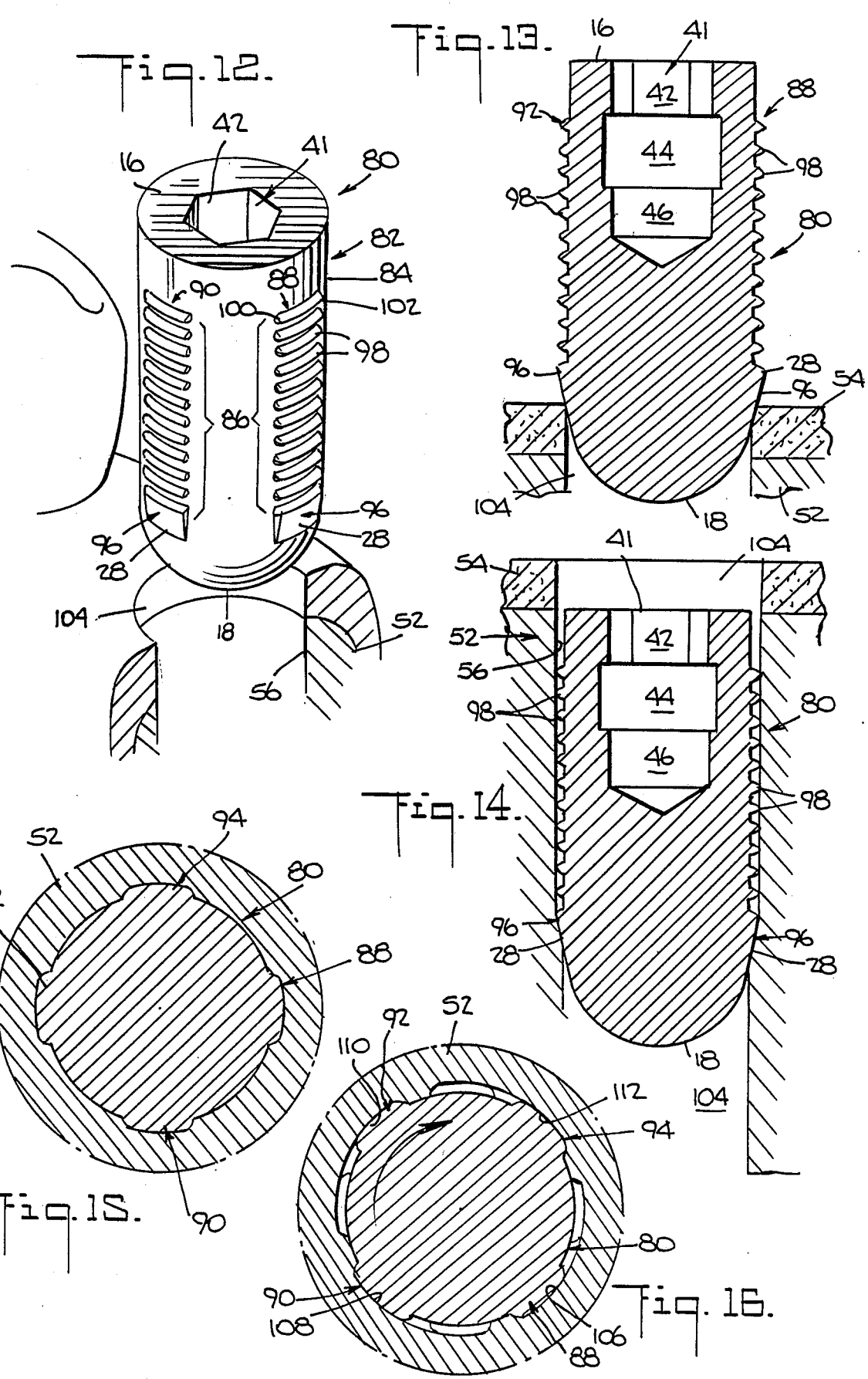

ORAL IMPLANT

BACKGROUND OF THE INVENTION

This invention relates to dental prostheses and more particularly to an oral implant that is installed in the jawbone for holding a dental prosthesis.

Oral implants serve as the foundation for a dental prosthesis and thus must have sufficient strength and stability to withstand the usual mandibular pressures. The structure of the implant and the manner in which it is installed in position in the jawbone are determinants in the ability of the implant to maintain its installed position over long periods of time.

Existing systems for installing an implant generally include a press-fitting of the implant in a drilled hole in the jawbone, a threading of the implant in a tapped hole in the jawbone, or a threading of the implant in a trephine drilled hole to accommodate a basket-type implant.

For example, U.S. Pat. No. 4,531,916 shows a dental implant that is press-fitted in a hole. Since the press-fit lacks a rigid attachment, making it vulnerable to movement, there is a need to provide apertures in the implant that permit ingrowth of bony tissue to assure a rigid attachment. Nevertheless, the implant as installed is vulnerable to movement and the potentials of nonhealing.

U.S. Pat. No. 4,259,072 shows a threaded implant that requires a tapping operation in the jawbone following the initial drilling of a precision hole. Although threading of the implant in the bone may provide more stability than a press-fit attachment, the implant is still vulnerable to movement. Thus it is usually necessary to rely on growth of new bone tissue and new connective tissue to further stabilize the installed position of the implant.

U.S. Pat. No. 4,431,416, shows a basket-type implant comprising an inverted cylindrical cage or basket that fits around a cylindrical bone core and into an annular recess formed by a trephine drill. The basket-type implant requires drilling of multiple holes and the breaking away of bone plug portions before drilling is resumed. Tapping of the hole to accommodate a threaded surface of the basket-type implant is also occasionally desired. The basket-type implant thus requires an extremely complex installation procedure that might discourage widespread use of such implant.

It is thus desirable to provide an oral implant that can be simply installed in a drilled hole, and does not rely on press-fitting, threading or trephine drilling to provide a stable, rigid positioning of the implant in the jawbone.

OBJECTS AND SUMMARY OF THE INVENTION

Among the several objects of the invention may be noted the provision of a novel oral implant, a novel oral implant which can be rigidly locked in position in the jawbone without threading or trephine drilling, a novel oral implant that can be easily installed yet rigidly locked into a stable position, a novel oral implant that resists movement or destabilization after being installed, a novel oral implant having novel projections that lock into the jawbone to form an undercut in the jawbone and a novel method of affixing an oral implant to the jawbone.

Other objects and features of the invention will be in part apparent and in part pointed out hereinafter.

The oral implant, in accordance with one embodiment of the invention, includes a generally cylindrical body with projecting means on predetermined portions of the cylindrical surface. The projecting means include projecting members that project a predetermined amount from the surface, have a predetermined radial extent, and are arranged in radially spaced longitudinal rows along quadrants of the cylindrical surface.

In a preferred embodiment of the invention the projecting members have a tapered surface that is tapered toward the longitudinal axis of the cylindrical body in a direction from a proximal end of the body member toward a distal end of the body member. The tapered surface is provided with flutes that define a row of longitudinal grooves. If desired, the grooves can be biased with respect to the longitudinal axis of the cylindrical body.

A lateral hole may be provided at the distal end of the body member and preferably passes through the most distally located projecting members on two opposite quadrants. A recess is provided at the proximal end of the cylindrical body, preferably in the shape of a hexagon for reception of a tightening tool as well as the dental prosthesis.

The oral implant is installed in a hole that substantially corresponds to the diameter of the cylindrical body, thus affording a press-fit against the cylindrical surface. After the cylindrical body is installed in the hole, a socket wrench is engaged in the hexagonal opening to twist the cylindrical body a predetermined amount. The projection members, when twisted, scrape into the bone surface in a manner similar to a breach lock mechanism forming an undercut in the bone. Because the fluted surfaces of the projections are embedded in the bone, the implant can resist outward displacement or twisting movement that might be caused by mandibular pressures.

Another embodiment of the invention includes projecting means with projecting members, as previously described, but without the fluted surface. In addition, the projecting means include radially spaced ridges on quadrants of the cylindrical surface. The ridges are longitudinally aligned with the tapered projecting members. The ridges have opposite radial ends and can be tapered from one radial end toward the other and can have a "V" shape or circular shape in longitudinal cross section.

The implant is installed in a drilled hole and twisted as previously described. The twisting enables the tapered projecting members and the radial ridges to breach into the bone.

Since the projecting members and ridges have no flutes, and since the ridges are radially aligned, there is no biasing movement of the implant in a longitudinal direction during the twisting operation. Thus the implant remains at the depth where it has been twisted and locked. Under this arrangement, the implant can be recessed in a drilled hole that has a greater depth than the longitudinal extent of the implant, without bottoming in the hole, thus assuring that the implant will not migrate into areas such as the sinus cavities.

The invention accordingly comprises the constructions and method hereinafter described, the scope of the invention being indicated in the claims.

DESCRIPTION OF THE DRAWINGS

In the accompanying drawings,

FIG. 5 is a sectional view of the implant in the fully installed position;

FIG. 6 is a sectional view taken on the line 6—6 of FIG. 5;

FIG. 7 is a perspective view of the implant being twisted into a locked position;

FIG. 8 is a sectional view similar to FIG. 6 showing the twisting of the implant into the locked position;

FIG. 9 is a sectional view similar to FIG. 7 showing the implant being twisted into a locked position;

FIG. 10 is a perspective view thereof prior to installation of a dental prosthesis in the implant;

FIG. 11 is an elevational view thereof partly shown in section with the dental prosthesis installed in the implant;

FIG. 12 is a perspective view of another embodiment of the invention;

FIG. 13 is a sectional view thereof prior to installation in a jawbone;

FIG. 14 is a view similar to FIG. 13 showing the implant fully installed in the jawbone;

FIG. 15 is a sectional view thereof taken on the line 15—15 of FIG. 14; and,

FIG. 16 is a view similar to FIG. 15 showing the implant being twisted into a locked position.

Corresponding reference characters indicate corresponding parts throughout the several views of the drawings.

DETAILED DESCRIPTION OF THE INVENTION

Figure 1:
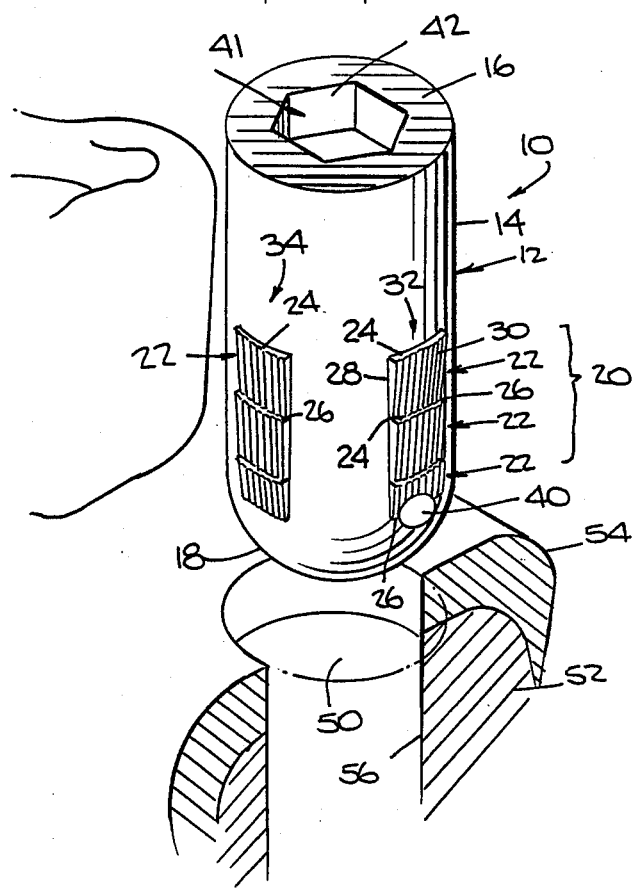
FIG. 1 is a perspective view of the oral implant incorporating one embodiment of the invention.

An oral implant incorporating one embodiment of the invention is generally indicated by the reference number 10 in FIG. 1.

Figure 2:
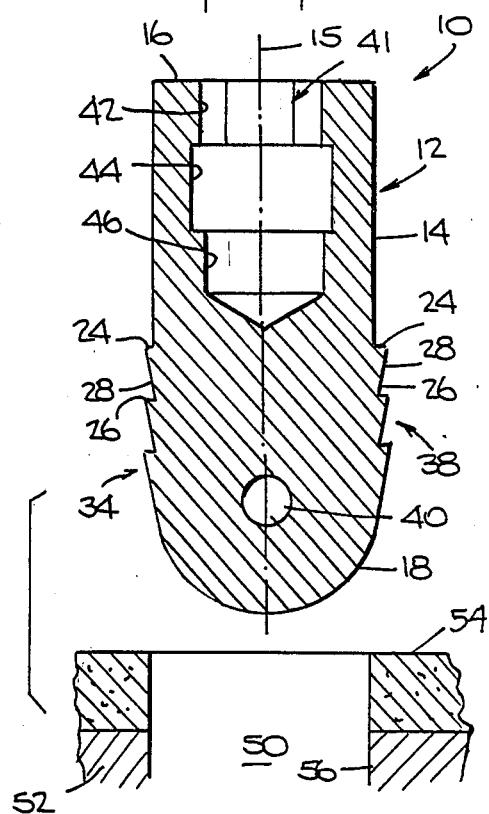
FIG. 2 is a simplified sectional view thereof prior to installation in a jawbone.

The oral implant 10 comprises a body member 12 having a generally cylindrical surface 14 with a longitudinal axis 15 (FIG. 2). The body member 12, which is formed of a suitable, biocompatible material such as titanium, is bullet-shaped, with a flat proximal end portion 16 and a spherically rounded distal end portion 18.

The cylindrical surface of the body member 1 is provided with projecting means 20 that include shingle-shaped projection members 22. The projecting members 2 each have a proximal end portion 24, a distal end portion 26 and a tapered surface 28 that tapers toward the longitudinal axis 15 in a direction from the proximal end portion 24 to the distal end portion 26. The tapered surface 28 is fluted with grooves 30 that have a longitudinal orientation or, if desired, a predetermined biased orientation with respect to the longitudinal axis 15.

The projection members 22 are preferably arranged in four longitudinal rows 32, 34, 36 and 38 of three projecting members 22 in longitudinally abutting relationship. The rows 32, 34, 36 and 38 are radially spaced 90° apart with respect to the longitudinal axis 15.

A lateral hole 40, formed in the body member 12, passes through the distal end 26 of the most distal projection member 22 in the rows 32 and 36 (FIG. 7). The proximal end portion 16 of the body member 12 is formed with a recess 41 having a hexagonal portion 42 and an enlarged intermediate annular channel 44 which functions as a clearance hole to facilitate fabrication (broaching) of the hexagonal portion 42. If desired, a lower portion 46 of the recess 41 can be formed with a circular cross section.

The precise dimensions of the implant 10 may vary since they are based on the dimensional characteristics of individual jawbones. Nevertheless, to exemplify the magnitudes being dealt with, the overall length of the body member 12 from the proximal end portion 16 to the distal end portion 26 can range from 7 mm. to 16 mm. The diameter of the cylindrical surface 14 can range from 3.5 mm. to 5 mm. The radial extent of the projecting members 22 is less than 45° and preferably approximately 36°. The angle of taper of the projecting members 22 is approximately 8° and the distance between the proximal end portion 24 and the distal end portion 26 of the projection member 22 is approximately 1.8 mm. The diameter of the lateral hole 40 is approximately 1.2 mm.

It should be noted that when the overall length of the body member 12 is 7 mm., it is preferable to use two projection members 22 in each of the rows 32, 34, 36 and 38. The use of three projection members 22 in a longitudinal row 32, 34, 36 and 38 becomes more feasible when the overall length of the body member is at least 10 mm.

In accordance with the foregoing dimensions, the projection member 22 projects approximately 0.25 mm. from the cylindrical surface 14 at the proximal end 24.

Figure 4:
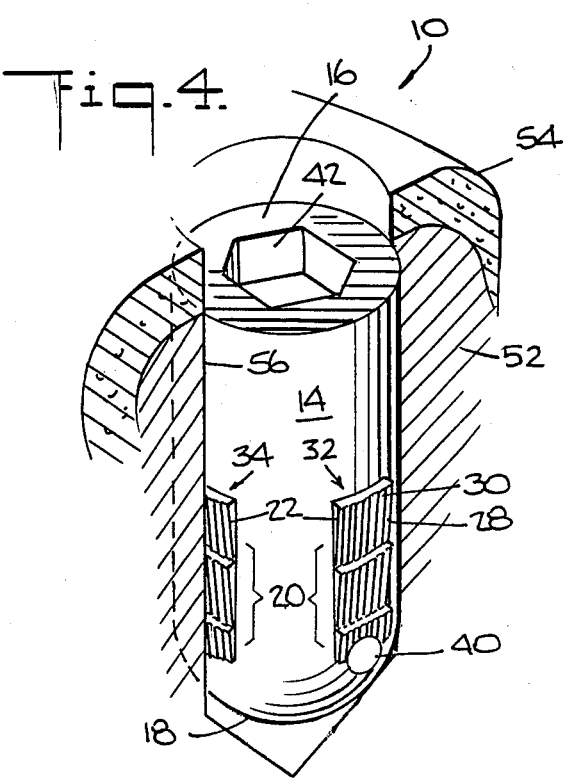
FIG. 4 is a perspective view of the implant fully installed in the jawbone.
Figure 3:
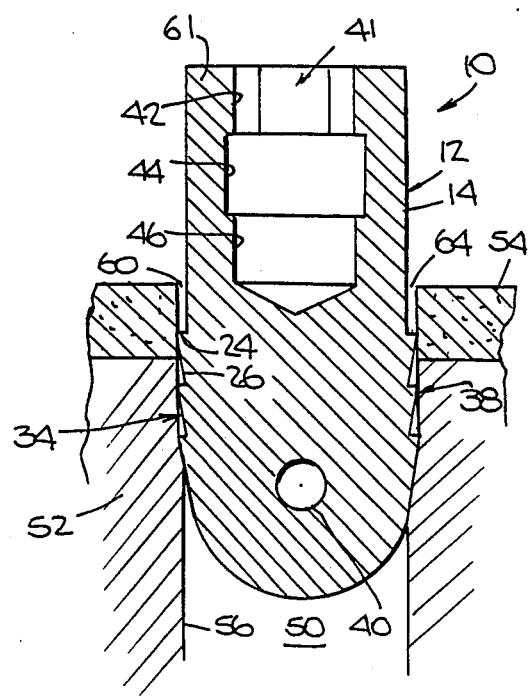
FIG. 3 is a view similar to FIG. 2 during installation of the implant into the jawbone.

In using the oral implant 10, the cylindrical surface 14 of the body member 12 is preferably coated with hydroxylapatite except for the proximal end surface 16. An installation hole 50 is drilled in the jawbone 52 through the gum layer 54. The hole 50 has a diameter that permits press-fitting of the cylindrical surface 14 against the bone surface 56 that defines the hole 50. Consequently, the projection members 22 will score channels 58, 60, 62 and 64 (FIG. 6) in the bone surface 56 as the body member 12 is driven into the hole 50. The depth of the hole 50 in the jawbone 52 should be sized to permit complete insertion of the body member 12 below the gum layer 54 as shown in FIGS. 4 and 7. The body member 12 can be driven into the hole 50 with a holding and driving tool 66.

The tool 66 includes an enlarged portion 67, a base portion 69, and an engagement stem 71 extending from the base portion 69 that is a hexagonal complement of the hexagonal recess portion 42. The engagement stem 71 is sized to provide a slight detent of the oral implant 10 when the stem 71 is received in the hexagonal recess portion 42. Thus the tool 66 can be used to hold and transport the implant 10 to the installation hole 50.

Once the implant 10 is aligned with the installation hole 50, the tool 66 is used to push the body member 12 into the hole 50 and, if desired, a mallet (not shown) can be used to tap the enlarged portion 67 to drive the base portion 69 against the proximal end 16 of the oral implant 10 and thereby urge the body member 12 into the installation hole 50 as shown in FIG. 11.

As the body member 12 is driven into the jawbone 52, the lateral hole 40 will accumulate bone scrapings due to the scraping away of bone tissue by the projection members 22.

After the oral implant 10 has been fully inserted in the jawbone 52, the driving tool 66 is removed and the body member 12 is rotated approximately 10° to 45° with a suitable rotational tool, such as a hexagonal wrench 73 (FIG. 9), thereby rigidly locking the implant 10 in place in a manner similar to that of a breach lock mechanism.

The twisting of the inserted body member 12 enables the fluted grooves 30 on the tapered surface of the projection member 22 to cut into the bone surface 56 from the channels 58, 60, 62 and 64 to form undercuts 68, 70, 72 and 74 (FIG. 8) that rigidly lock the body member 12 in position.

The oral implant 10 is then ready for a healing cap 75, shown in dotted outline in FIG. 7, and the suturing of the gum layer 54. The healing cap 75 is a silicone plug that is inserted into the recess 42 covering the proximal end 16 of the implant 10, to prevent bone from growing over the implant. The gum 54 is then sutured over the healing cap 75 for a predetermined healing period.

After the healing process is completed, a dental prosthesis is installed in the recess 41 in a known manner.

Another embodiment of the oral implant is generally indicated by the reference number 80 in FIG. 12.

The oral implant 80 includes a body member 82 with a cylindrical surface 84 having projecting means 86. The projecting means 86 are arranged in quadrants of the cylindrical surface 84 and include four longitudinal rows 88, 90, 92 and 94.

The projecting means 86 include a shingle-shaped projecting member 96 formed at the distal end of each row 88, 90, 92 and 94. The projecting member 96 is similar in structure to the projecting member 22 but does not include a fluting of the tapered surface 28.

The longitudinal rows 88, 90, 92 and 94 further include longitudinally spaced ridges 98 having the same radial extent as the projecting members 96 and a longitudinal thickness which is of lesser magnitude than the radial extent.

The ridges 98 in one longitudinal row such as the row 88 are radially aligned with corresponding ridges 98 in the other longitudinal rows 90, 92 and 94. Thus, for example, the most proximal ridge 98 in the row 88 is at the same longitudinal level as the most proximal ridge 98 in the rows 90, 92 and 94. The ridges 98 in longitudinal cross section can have any selected shape such as a "V" shape or a rounded shape. In addition, the ridges 98 can be tapered from one radial end such as 100 in FIG. 12 to the other radial end 102, the taper of all the ridges 98 running in the same radial direction.

Although not shown, the implant 80 can include a lateral hole (not shown) identical to the lateral hole 40 of the oral implant 10, at the distal end of the projection members 96 in the row 88 and 92.

The oral implant 80 is installed in a manner similar to that previously described for the oral implant 10. Thus the wrench 66 is used to twist the implant 80 after it has been fully inserted in an installation hole 104 of the jaw bone 52.

Since there are no flutes or grooves on the projecting members 96 or the ridges 98, the implant 80 is not biased to move in a longitudinal direction during the twist lock operation. Thus, upon twisting the implant 80 after insertion in the jawbone 52, there will be no upward or downward longitudinal movement of the implant 80.

Twisting of the implant 80 causes the projecting members 96 to form undercuts in the bone that lock the implant 80 in position in the hole 104. Since the tapered ridges 98 also lock into the bone wall 56 forming undercuts 106, 108, 110 and 112 (FIG. 16), the direction of twist for this embodiment is predetermined and is from the larger tapered end 102 of the ridge 98 to the smaller end 100.

The implant 80 can thus be twisted and locked in position in the hole 104 at the depth where the implant 80 is recessed. If the implant 80 is placed in a drilled hole 104 that is deeper than the longitudinal extent of the implant, the twist lock capability without longitudinal movement ensures that the implant 80 will not migrate into other areas such as the sinus cavities.

Some advantages of the present invention evident from the foregoing description include an oral implant that can be easily installed in a drilled hole in a jawbone. The implant, once twisted, is rigidly locked in position due to the formation of an undercut in the jawbone by projections formed on the implant. There is no need to provide tapping, threading or trephine drilling of the drilled hole in the bone and only one hole of one size need be drilled into the bone.

The lateral hole 40 at the distal end of the implant, in addition to accommodating bone scrapings, also provides an entrance for bone growth to further enhance the grip of the jawbone on the implant.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An oral implant comprising
   (a) a body member having a generally cylindrical surface and a longitudinal axis surrounded by said cylindrical surface, said cylindrical surface being without an exterior spiral thread,
   (b) a plurality of shingle-shape projecting members provided on a predetermined portion of said cylindrical surface to project a predetermined amount from said surface, said projecting members each having a predetermined radial extent with respect to said longitudinal axis of less than 360 degrees and a predetermined longitudinal extent, said projecting member each having proximal and distal end portions with respect to said longitudinal axis, said projecting members each having a tapered surface that tapers toward said longitudinal axis in a direction from said proximal end portion to said distal end portion, said tapered surface having substantially longitudinally directed flutes, and
   (c) means for holding a dental prosthesis.

2. The oral implant as claimed in claim 1 wherein said predetermined radial extent of said projecting member is less than 90 degrees.

3. The oral implant as claimed in claim 1 wherein said projecting members are in a longitudinal arrangement on said cylindrical surface.

4. The oral implant as claimed in claim 3 wherein said longitudinally arranged projecting members include a most distally arranged projecting member having a distal end portion and a through-hole extending laterally with respect to said longitudinal axis through the distal end portion of the most distally arranged projection.

5. The oral implant as claimed in claim 1 wherein at least a couple of said projecting members are radially spaced 90 degrees apart on said cylindrical surface.

6. The oral implant as claimed in claim 5 wherein the predetermined radial extent of the projecting members is less than 45°.

7. The oral implant as claimed in claim 1 wherein the angle of taper of said tapered surface is greater than 5° and less than 12°.

8. The oral implant as claimed in claim 1 wherein said body member has a proximal end and a distal end and said distal end is hemispherically rounded.

9. The oral implant as claimed in claim 1 wherein said projecting member include at least one ridge having a predetermined radial extent and a predetermined longitudinal extent, the magnitude of the radial extent exceeding the magnitude of the longitudinal extent.

10. The oral implant as claimed in claim 9 wherein said member include several of said ridges radially spaced on said cylindrical surface.

11. The oral implant as claimed in claim 10 wherein said several ridges are radially spaced 90 degrees apart on said cylindrical surface, in longitudinal alignment with said projecting members, said several ridges being longitudinally spaced a predetermined amount from each other.

12. The oral implant as claimed in claim 11 wherein said ridges have opposite radial ends and are tapered from one radial end to the other radial end.

13. The oral implant as claimed in claim 9 wherein said ridges, in longitudinal cross section have a "V" shape.

14. The oral implant as claimed in claim 9, wherein said ridges, in longitudinal cross section have a rounded shape.

15. A method of affixing a generally cylindrical oral implant with proximal and distal end portions to a bone comprising
  (a) drilling a hole in the bone with a diameter substantially corresponding to the cylindrical diameter of the oral implant to permit press-fitting of the implant in the bone, the depth of the hole substantially corresponding to the longitudinal extent of the implant,
  (b) forming shingle-shaped projections on the surface of the implant that are of shorter longitudinal extent than the implant and that taper toward the cylinder axis of the implant in a direction from the proximal end portion to the distal end portion, the amount of projection being selected to permit the projections to cut into the bone as the implant is press-fitted into the hole,
  (c) radially spacing a plurality of the shingle projections of the surface of the implant,
  (d) press-fitting the implant in the hole such that substantially the entire longitudinal extent of the implant is recessed in the jawbone,
  (e) twisting the implant in the hole after it has been press-fitted to cause the projections to breach into the bone surface of the hole thereby locking the implant in the hole.

16. The method as claimed in claim 16 including forming flutes on the tapered surface of the projections.

17. The method as claimed in claim 15 including forming preselected numbers of radially spaced, radially extending ridges on the cylindrical surface and spacing the ridges to permit breaching thereof in the bone surface of the hole when the implant is twisted.

* * * * *